(12) United States Patent
Yu et al.

(10) Patent No.: US 8,294,757 B2
(45) Date of Patent: Oct. 23, 2012

(54) IMAGING CHAMBER WITH WINDOW AND MICRO-NEEDLE PLATFORM MAGNETICALLY BIASED TOWARD EACH OTHER

(75) Inventors: Hanry Yu, Singapore (SG); Yuet Mei Khong, Singapore (SG); Hwa Liang Leo, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 478 days.

(21) Appl. No.: 12/666,631

(22) PCT Filed: Jun. 26, 2008

(86) PCT No.: PCT/SG2008/000224
§ 371 (c)(1),
(2), (4) Date: Dec. 23, 2009

(87) PCT Pub. No.: WO2009/002273
PCT Pub. Date: Dec. 31, 2008

(65) Prior Publication Data
US 2010/0208049 A1      Aug. 19, 2010

Related U.S. Application Data

(60) Provisional application No. 60/929,402, filed on Jun. 26, 2007.

(51) Int. Cl.
*G02B 21/26* (2006.01)
*H04N 7/18* (2006.01)

(52) U.S. Cl. .................. 348/77; 348/79; 435/4

(58) Field of Classification Search ........... 348/77, 348/79; 435/4
See application file for complete search history.

(56) References Cited

U.S. PATENT DOCUMENTS

| 5,614,412 A | 3/1997 | Smith et al. |
|---|---|---|
| 6,037,171 A | 3/2000 | Larsson |
| 6,508,766 B2 | 1/2003 | Sato et al. |

(Continued)

FOREIGN PATENT DOCUMENTS

WO    WO99/33492    7/1999

(Continued)

OTHER PUBLICATIONS

Focht, "Live-Cell Microscopy: Environmental Control for Mammalian Specimens", Nature Biotechnology, 1996, pp. 361-362, vol. 14.

(Continued)

*Primary Examiner* — Khanh Dinh
(74) *Attorney, Agent, or Firm* — Klarquist Sparkman, LLP (57) ABSTRACT

A device for imaging a tissue culture comprises a chamber for housing a tissue to be cultured and imaged. The chamber comprises a transparent window. The device also includes a platform facing the window. Micro-needles are mounted on the platform and are connected for fluid communication with a fluid source. The platform and the window are magnetically biased toward each other to press the micro-needles into a tissue sandwiched between the window and platform for injecting a fluid into the tissue. One or more spacers are placed between the platform and the window for preventing over-compression of the tissue by the platform and the window. During use, a fluid is supplied to the tissue through the needles from the fluid source and the tissue is imaged through the window of the chamber.

22 Claims, 6 Drawing Sheets

U.S. PATENT DOCUMENTS

| | | | |
|---|---|---|---|
| 6,753,005 | B1 | 6/2004 | Pietronigro et al. |
| 7,262,068 | B2 | 8/2007 | Roy et al. |
| 7,393,924 | B2 * | 7/2008 | Vitaliano et al. ............... 530/350 |
| 7,740,612 | B2 * | 6/2010 | Hochman ..................... 604/121 |
| 2004/0235145 | A1 | 11/2004 | Cima et al. |
| 2005/0267552 | A1 * | 12/2005 | Conquergood et al. ......... 607/96 |
| 2006/0134600 | A1 * | 6/2006 | Fuhr et al. .......................... 435/4 |
| 2007/0141163 | A1 * | 6/2007 | Vitaliano et al. ............... 424/490 |
| 2010/0208049 | A1 * | 8/2010 | Yu et al. .......................... 348/77 |

FOREIGN PATENT DOCUMENTS

| | | |
|---|---|---|
| WO | WO02/15960 A2 | 2/2002 |
| WO | WO2006/041414 A1 | 4/2006 |

OTHER PUBLICATIONS

Ho et al., "Mini chamber system for long-term maintenance and observation of cultured calls"; Biotechniques, 2005, pp. 267-272, vol. 28, No. 2.

Blau et al, "Prototypeof a novel autonomous perfusion chamber for long-term culturing and in situ investigation of various cell types", Journal of Biochemical and Biophysical Methods, 2001, pp. 16-27, vol. 50.

Kaplan et al., "A rapid-low perfusion chamber for high-resolution microscopy"; Journal of Microscopy, 1996, pp. 286-297, vol. 181, Pt. 3.

Kasparov et al., "Dynamic confocal imaging in acute brain slices and organotypic slice cultures using a spectral confocal microscope with single photon excitation", Experimental Physiology, 2002, pp. 714-724, vol. 87.6.

Passeraub et al., "Design, Microfabrication and Analysis of a Microfluidic Chamber for the Perfusion of Brain Tissue Slices", Biomedical Microdevices, 2003, pp. 147-165, vol. 5:2.

Khong et al., "A Novel Intra-tissue Perfusion Culture of Thick Liver Slices", in Proceedings of Conference on Regenerate World Congress on Tissue Engineering and Regenerative Medicine, Pittsburgh, USA, Apr. 25-27, 2006.

Khong et al., "Novel Intra-Tissue Perfusion System for Culturing Thick Liver Tissue", Tissue Engineering, 2007, pp. 2345-2356, vol. 13.

Grayson et al., "A BioMEMS Review: MEMS Technology for Physiologically Integrated Devices", Proceedngs of the IEEE, 2004, pp. 6-21, vol. 92, No. 1.

International Search Report and Written Opinion, mailed Jul. 31, 2008, in related PCT Application No. PCT/SG2008/000224.

International Preliminary Report on Patentability mailed Jun. 16, 2009, in related PCT Application No. PCT/SG2008/000224.

* cited by examiner

IMAGING CHAMBER WITH WINDOW AND MICRO-NEEDLE PLATFORM MAGNETICALLY BIASED TOWARD EACH OTHER

CROSS-REFERENCE TO RELATED APPLICATION

This application claims the benefit of U.S. provisional application No. 60/929,402, filed Jun. 26, 2007, the contents of which are incorporated herein by reference.

FIELD OF THE INVENTION

The present invention relates to imaging chambers, particularly to imaging chambers with micro-needles for intra-tissue perfusion.

BACKGROUND OF THE INVENTION

WO 2006/041414 to Yu et al., entitled "Tissue System and methods of use" and published Apr. 20, 2006, discloses a tissue system for culture and perfusion, which includes a micro-needle chamber. The chamber includes a base, a membrane placed on the base, a micro-needle platform having micro-needles, and a top cover. A tissue is placed on and held by the membrane. The micro-needle platform is placed on the tissue. The top cover encloses the chamber and is connected to a perfusion circuit. The chamber is fixed together using screws and is connected to the perfusion circuit. A fluid is injected into the tissue through the needles. This chamber can be improved.

SUMMARY OF THE INVENTION

In accordance with an aspect of the present invention, there is provided a device for imaging a tissue culture. The device comprises a chamber for housing a tissue to be cultured and imaged therein. The chamber comprises a transparent window. The device also includes a platform facing the window. Micro-needles are mounted on the platform and are connected for fluid communication with a fluid source. The platform and the window are magnetically biased toward each other to press the micro-needles into a tissue sandwiched between the window and platform for injecting a fluid into the tissue. One or more spacers are placed between the platform and the window for preventing over-compression of the tissue by the platform and the window. The chamber may comprise a well-shaped base and a cover for covering the base. The window may form a part of the base. A first magnet may be attached to the platform and a second magnet may be attached to the base. The first and second magnets attract each other thus biasing the platform and the window toward each other. The first magnet may comprises a first set of disc magnets, and the second magnet may comprise a second set of disc magnets. The base may comprise a Petri dish. The micro-needles may comprise seven needles. The spacer may have a thickness of about 1 mm. The tissue may have a thickness of about 1 mm or more. The device may also comprise an inlet in fluid communication with the needles for supplying a fluid to the tissue, and an outlet for discharging a fluid from the chamber. The window may be formed of glass. The window may comprise a transparent polymer. The platform may be formed of a polymer. The spacer(s) may be attached to the platform. A plurality of spacers may be provided. The chamber may have a generally cylindrical external shape.

In accordance with another aspect of the present invention, there is provided a method of operating the device described in the preceding paragraph. In this method, a tissue is placed on the window. The platform is placed on the tissue with the needles contacting the tissue. The platform and the window are magnetically biased toward each other, thus pressing the needles into the tissue. A distance is maintained between the platform and the window with the spacer. A fluid is supplied to the tissue through the needles from the fluid source. The tissue is imaged through the window of the chamber. A waste fluid may be discharged from the chamber, such as through the outlet. The tissue may be imaged with a camera or a microscope. The microscope may be an inverted microscope. The microscope may be a confocal microscope. The tissue may be monitored over a period of time.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
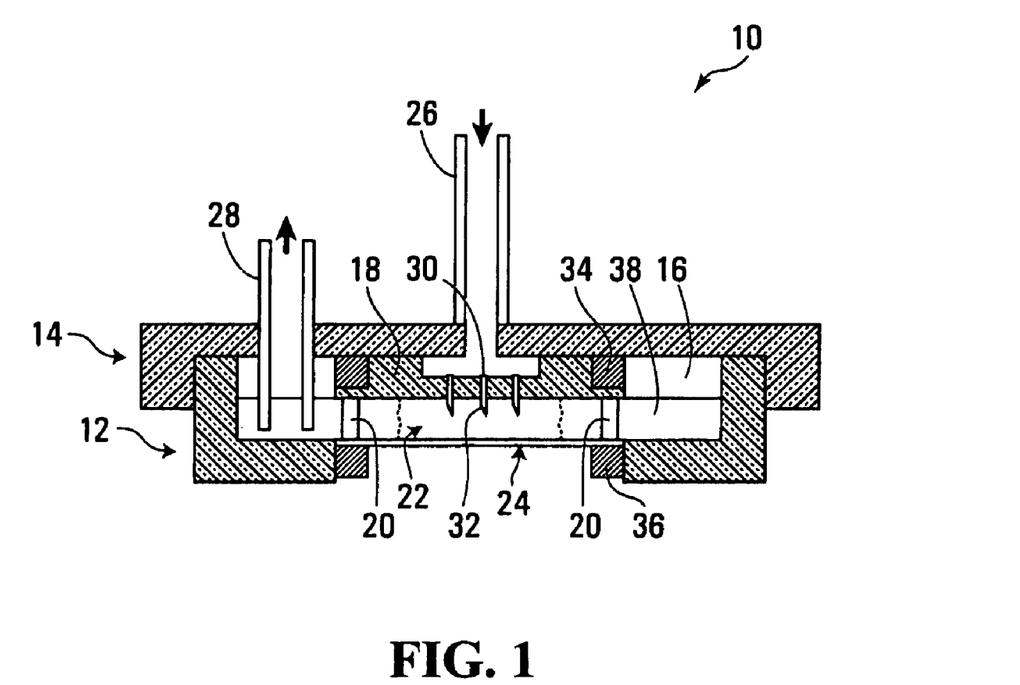
FIG. 1 is a cross-sectional view of an imaging chamber, exemplary of an embodiment of the present invention.
Figure 2:
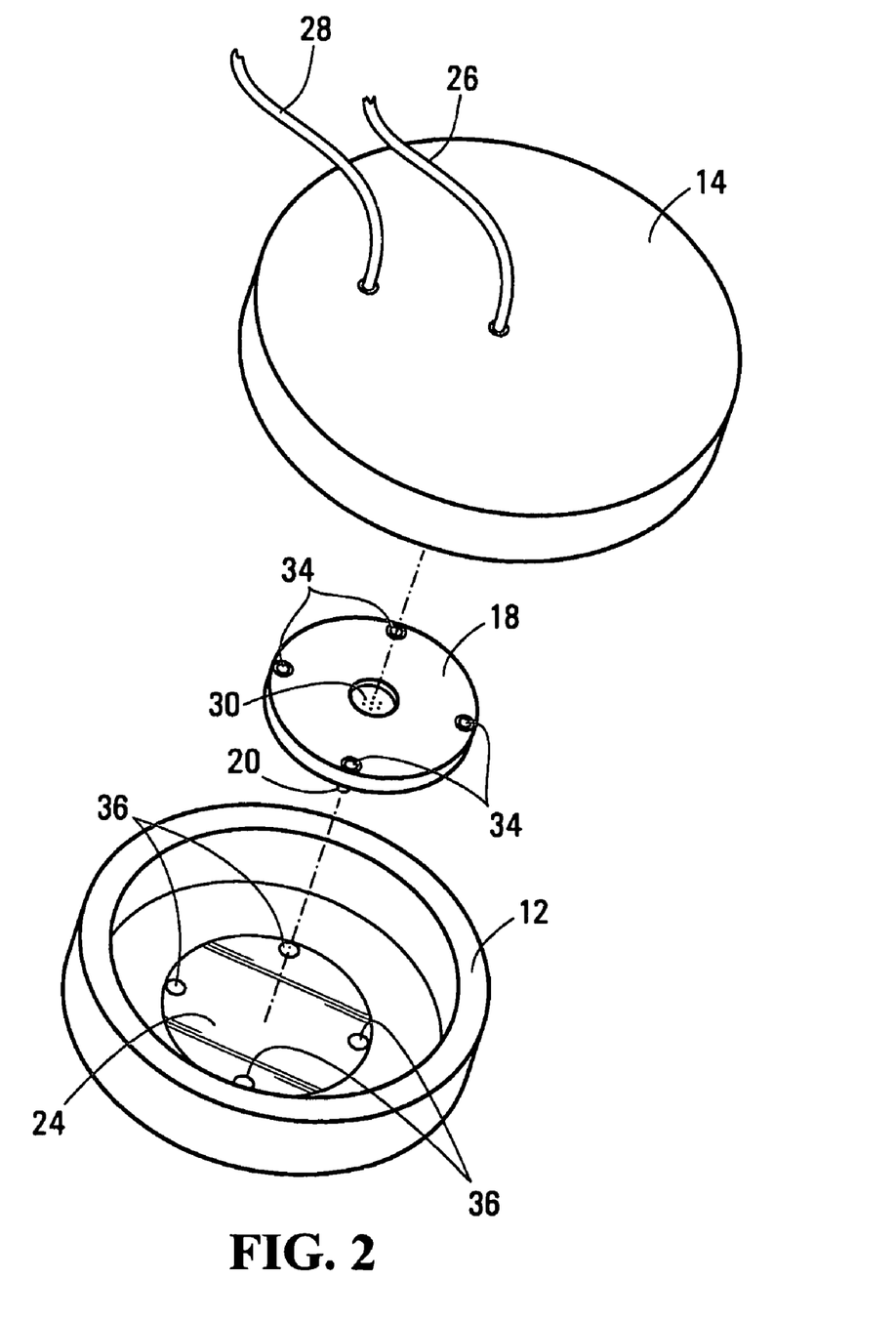
FIG. 2 is an exploded perspective view of the image chamber of FIG. 1.
Figure 3:
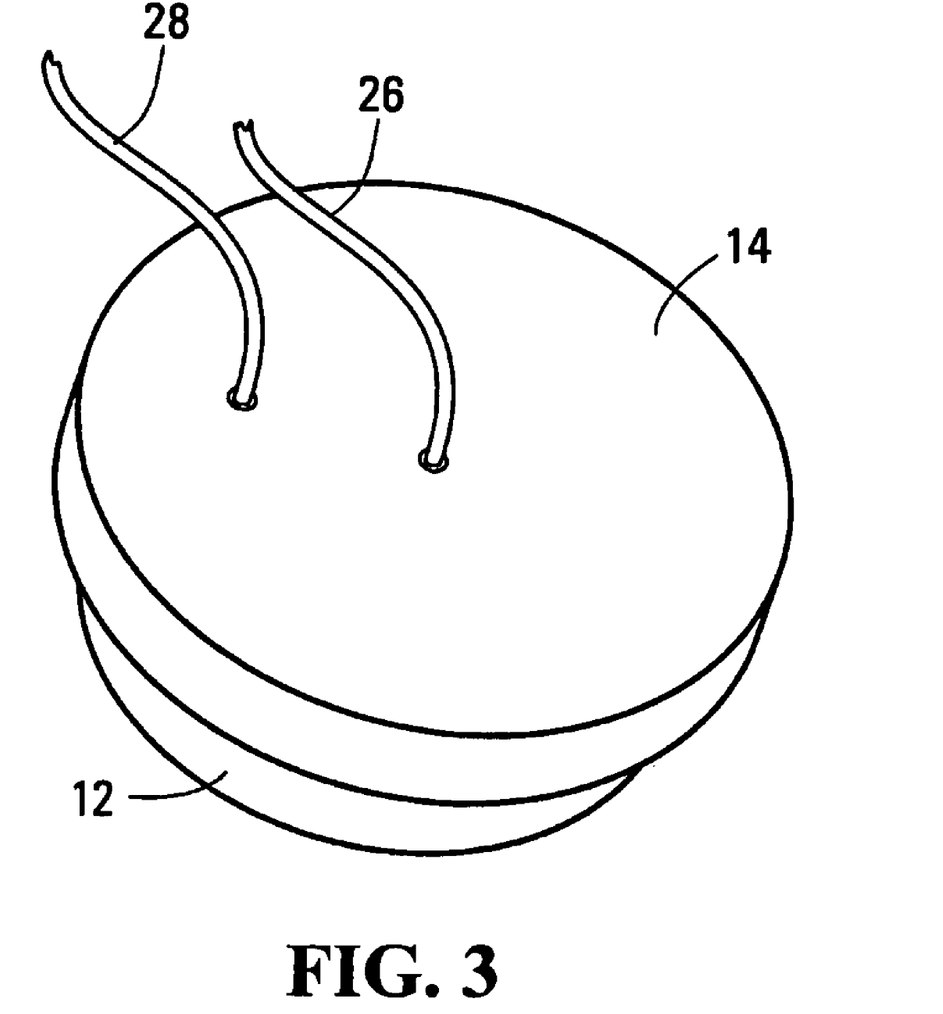
FIG. 3 is a perspective view of the image chamber of FIG. 1.

FIG. 1 is a cross-sectional view of an imaging chamber 10, exemplary of an embodiment of the present invention. Perspective views of image chamber 10 are shown in FIGS. 2 and 3.

Chamber 10 includes a base 12 and a cover 14, which when assembled, define an enclosed chamber volume 16. A micro-needle platform 18 is mounted between base 12 and cover 14. A spacer 20 is disposed between platform 18 and base 12, which are biased toward each other magnetically. A tissue 22 may be disposed between platform 18 and base 12 during use. The spacer 20 is positioned and sized to prevent tissue 22 from being over-compressed by base 12 and platform 18.

Base 12 includes a transparent window 24, which may be made of, for example, glass or a polymer material suitable for forming a cover-slip for microscopes. Thus, tissue 22 may be continuously monitored or imaged through window 24 during use, with an imaging device (not shown), such as a camera or a microscope which may be an inverted microscope. Base 12 may have a well-shape. In some embodiments, base 12 may have a general shape similar to a Petri dish. An existing Petri dish may be used, or adapted, to form base 12 in some applications.

A fluid inlet 26 and a fluid outlet 28 are provided for feeding fluids to and extracting fluids from chamber 10 respectively. As illustrated in the embodiment shown in FIG. 1, inlet 26 and outlet 28 may pass through cover 14. In different embodiments, outlet 28 may pass through a side wall of base 12 instead of cover 14.

Cover 14 may be transparent and may be made of any suitable material.

Base 12 and cover 14 may be sized so that when cover 14 covers base 12 the side walls thereof frictionally engage each other, which may provide a sealing engagement for preventing contamination. The sizes and shapes of the side walls of base 12 and cover 14 are selected such that the assembled base 12 and cover 14 can move axially relative to each other (e.g. telescopically) during use.

Needle platform 18 includes a plurality of micro-needles 30 for injecting one or more fluids into tissue 22. Each micro-needle 30 has a sharp tip 32 for conveniently entering into tissue 22 and provides a conduit therein that is in fluid communication with inlet 26. In one embodiment, there may be seven needles. In other embodiments, there may be more or less needles. Needles 30 may be made of any suitable material. In one embodiment, they may be made of stainless steel. The needles may have suitable dimensions depending on the particular application. In one embodiment, they have an external diameter of about 0.3 mm and an internal diameter of about 0.15 mm, a length of about 5 mm and a 30° bevel point at the tips 32. The sharp tips 32 of the needles 30 face tissue 22 sandwiched between base 12 and platform 18 so needles 30 can be pressed into the tissue 22 when window 24 and platform 18 are biased toward each other. Needles 30 are in fluid communication with inlet 26 during use to inject the input fluid(s) such as nutrients or the like, which are received from inlet 26, into an internal region of tissue 22. Needles 30 may be arranged in any suitable pattern on platform 18 depending on the application. For example, the number and density of needles 30 may be selected to suit a particular requirement or to closely mimic a real environment. Suitable needles are commercially available, such as from Micro-Group, Inc.

In one embodiment, platform 18 may be removably attached to cover 14. The attachment may be effected in any suitable manner, as can be understood by persons skilled in the art. In some applications, it may be convenient when platform 18 is detachable from cover 14, for example, to facilitate treatment, such as priming, of internal surfaces of chamber 10 and needles 30. In other embodiments, platform 18 may be detached from cover 14 and be supported in another suitable manner. It may be convenient if needle platform 18 is movable toward or away from window 24 during use, to allow for tissues of different thickness or to position the needle tips 32 at different depths in tissue 22, depending on the particular application. For example, different sets of spacers 20 with different heights may be provided for use with tissues of different thickness.

In one embodiment, two sets of magnets 34, 36 may be provided. One set of magnets 34 are attached to platform 18. The other set of magnets 36 are attached to base 12, such as at locations adjacent window 24. Magnets 34, 36 may be attached in any suitable manner. For example, they may be embedded in, or attached by adhesive to, platform 18 or base 12. Magnets 34 and 36 are configured and mounted to attract each other so that they will bias window 24 and platform 18 toward one another. Magnets 34, 36 may be generally disc-shaped. Other shapes are also possible in different embodiments.

Spacers 20 may have a thickness (or height as seen in FIG. 1) of about 1 mm and may be attached to the surface of platform 18 that faces window 24. Spacers 20 may be semi-resilient to allow some compression of the tissues. Spacers 20 may be attached to either platform 18 or base 12, or both of them. Spacers 20 may also be unattached. For example, spacers 20 may include beads or blocks for spacing platform 18 and window 24 apart. The thickness of spacers 20 may vary. In one embodiment, the thickness of spacers 20 may be selected to provide a sufficient distance between platform 18 and window 24 so that tissue 22 does not contact the bottom surface of platform 18 (but in contact with needles 30) during culturing and imaging. The space between platform 18 and tissue 22 can allow fluid communication therethrough.

Chamber 10 may be formed using any suitable manufacturing technique. For example, base 12, cover 14 and platform 18 may be formed of a transparent FullCure 720™ material and may be shaped using a lithographic technique such as using a three-dimensional (3D) PolyJet™ printer (Eden 350™).

Chamber 10 may include other optional components (not shown) and may include further fluid conduits (not shown) for various purposes.

Chamber 10, including base 12, cover 14, and platform 18 may be generally circular or cylindrical shaped, or have another general shape such as square, rectangular or the like. Magnets 34 and 36 and spacer 20 may be ring-shaped or have another shape.

In use, cover 14 and platform 18 is initially removed from base 12. The surfaces of various components of chamber 10 may be pre-treated such as primed before use. In this regard, it may be convenient that needles 30 can be separated from cover 14 so that they can be separately primed or cleaned. Cleaning and priming the internal surfaces of chamber 10 may have various benefits such as reducing bubbles in the input fluid.

Tissue 22, such as a slice of liver tissue, is placed on window 24 of base 12. The tissue slice may have a thickness of about 1 mm. The tissue slice may also be thicker or thinner. Platform 18 is then placed on top of tissue 32 with needles 30 facing tissue 22. Spacers 20 are placed between platform 18 and window 24 (or base 12) to define a minimum distance therebetween. Platform 18 and window 24 are biased toward each other by the attractive magnetic force between the magnets 34 and 36. As platform 18 and window 24 move toward each other, needles 30 are pressed into tissue 22 to a selected depth. As can be appreciated, the total magnetic force between the magnets 34 and 36 should be sufficiently strong to press the needles into tissue 22. The minimum distance between platform 18 and window 24 is determined by the thickness (height) of spacers 20. Spacers 20 are selected or adjusted, depending on what type of spacers 20 are used, to ensure that tissue 22 is not over-compressed and that tips 32 of needles 30 are at a desired region/depth in tissue 22. For example, when the tissue slice is about 1 mm thick, the spacers 20 may also be about 1 mm high. The exposed lengths of needles 30 may be selected or adjusted for achieving the desired depth inside tissue 22.

After the needles 30 are pressed to the desired depth, the attractive magnetic force between magnets 34 and 36 continues to bias platform 18 and window 24 toward each other, thus stabilizing the assembly in chamber 10.

As can be appreciated, it is not necessary to use screws to secure platform 18 and base 12 (window 24) in place relative to each other. With the use of spacer 20, over-compression of the tissue can also be avoided. Image chamber 10 is easy to assemble or disassemble and is convenient to use.

Chamber 10 may be filled with a suitable culturing medium 38 or another fluid.

Cover 14 is put on base 12 to close chamber 10.

Inlet 26 is connected to a perfusion circuit (not shown) for supplying input fluids to chamber 10 during operation, thus providing a fluid source for needles 30. Fluids such as nutrients or the like may be fed to tissue 22 through inlet 26 and needles 30.

Outlet 28 is connected to a disposal device (not shown) for disposing waste and other materials discharged from chamber 10.

The fluid flow rate for various input and output fluids may be adjusted using the perfusion circuit to maintain a desired fluid contents and refresh rate in chamber 10 and in tissue 22.

An imaging device (not shown) may be placed outside window 24 to monitor or image tissue 24 over a period of time. The imaging or monitoring may be conveniently carried out over an extended period of time continuously. The culturing medium and other fluids may be continuously supplied to chamber 10, without removing the imaging device or disassembling chamber 10. The imaging device may include a digital camera, a microscope such as such as an inverted microscope or a confocal microscope, or the like.

As can be appreciated, when image chamber 10 or base 12 has a general shape and dimension that resembles a Petri dish, it can conveniently fit into the holder of a conventional microscope that is designed to hold a Petri dish.

Image chamber 10 may also be shaped to fit into a culturing platform that provides a controlled $CO_2$ and temperature environment for supporting tissue viability. Such a culturing platform may be commercially available. As can be appreciated, a controlled environment may be necessary in some applications to ensure tissue survival.

Figure 4:
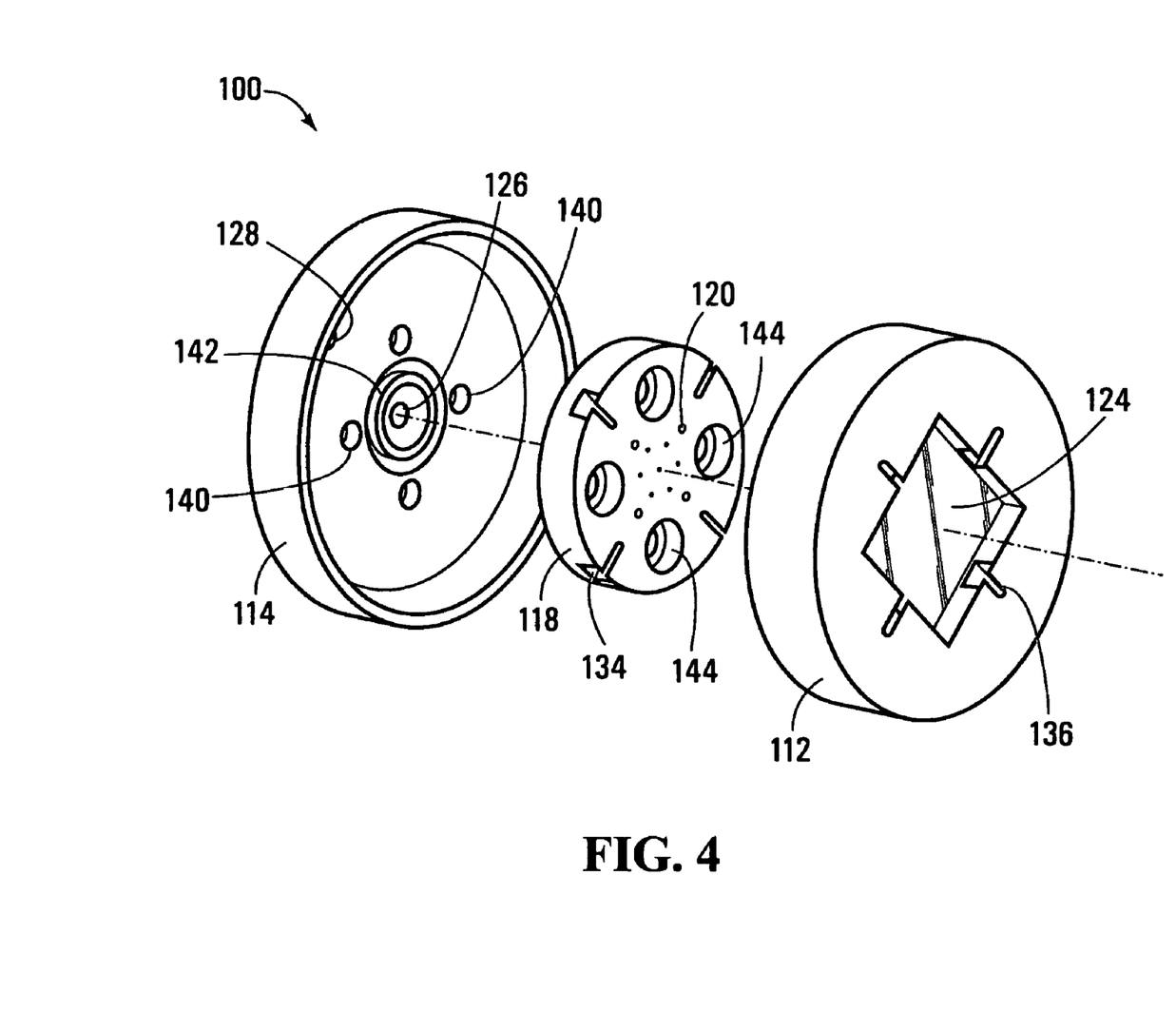
FIG. 4 is an exploded perspective view of another image chamber, exemplary of an embodiment of the present invention.

FIGS. 4 to 7 show another image chamber 110, exemplary of an embodiment of the present invention. As shown in FIG. 4, image chamber 110 includes a base 112, a cover 114, and a needle holder 118.

Figure 5:
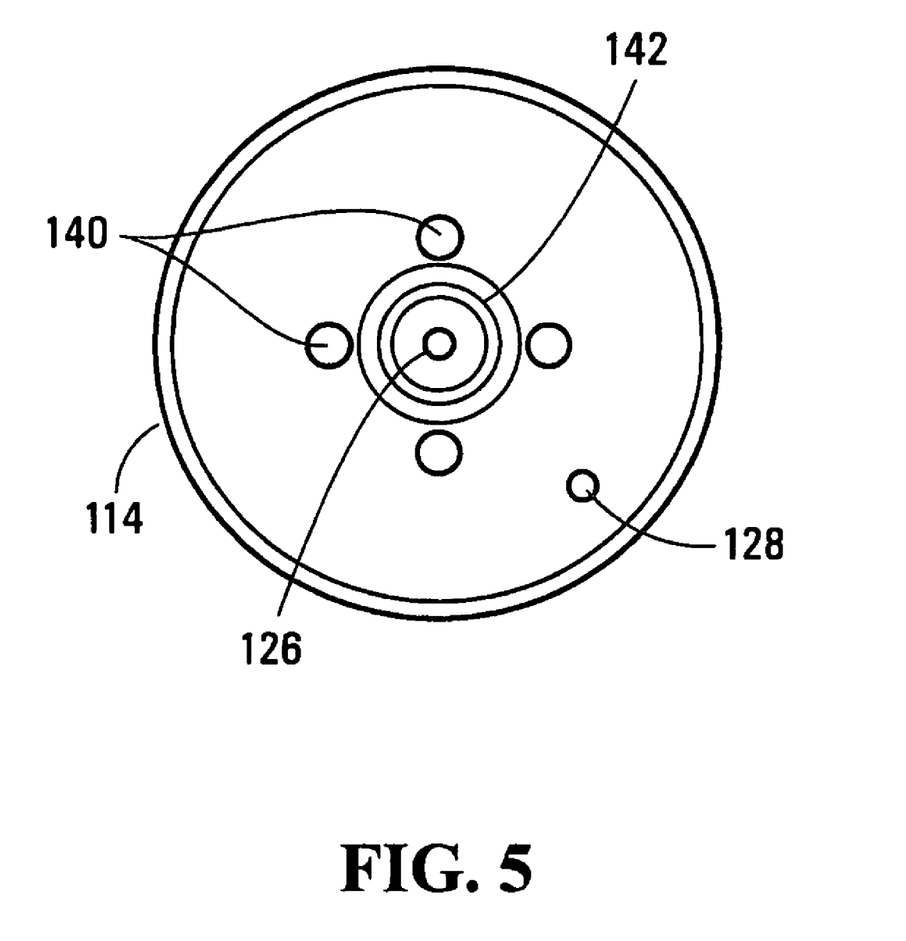
FIG. 5 is a top plan view of the cover of the image chamber of FIG. 4.

As shown in FIGS. 4 and 5, cover 114 has an inlet opening 126 for mounting an inlet conduit (not shown) and an outlet opening 128 for mounting an outlet conduit (not shown). Cover 114 also has four openings 140, and a circular ridge 142 around inlet opening 126, the use of which will become clear below. Cover 114 may be transparent.

Figure 6:
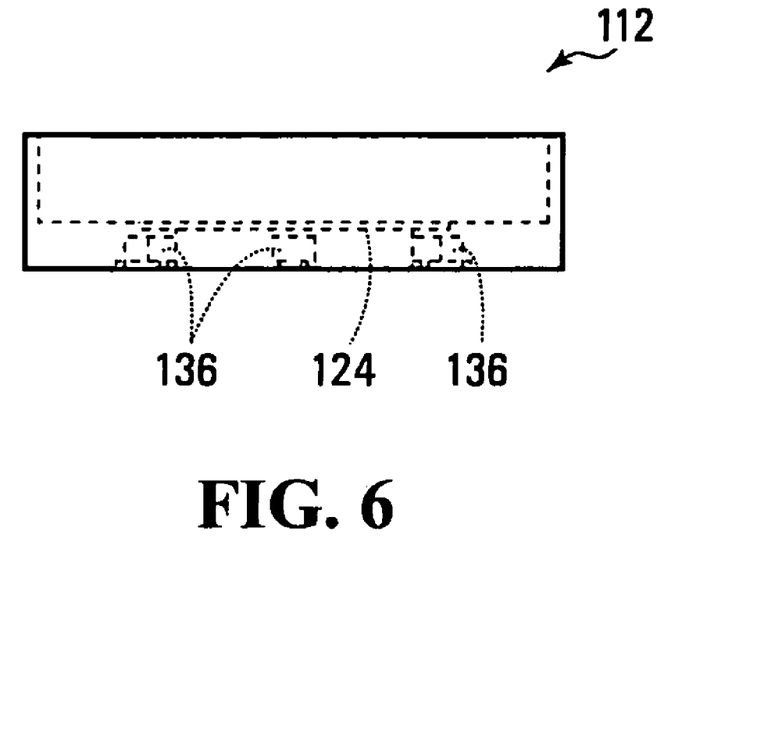
FIG. 6 is a side elevation view of the base of the image chamber of FIG. 4.

As shown in FIGS. 4 and 6, base 112 has the general shape of a Petri dish and defines a well. A generally square-shaped glass window 124 is provided at the bottom of the well defined by base 112. Four slots 136 are provided adjacent window 24 for receiving and housing magnets (not shown). Base 12 may be transparent.

Figure 7:
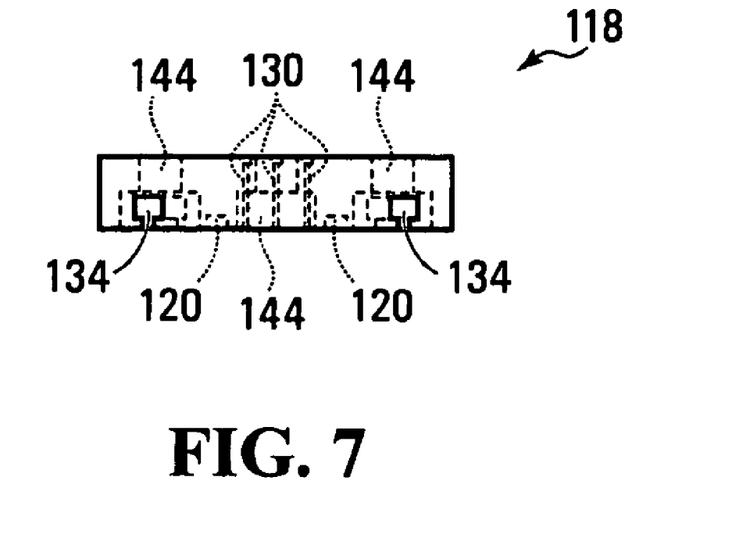
FIG. 7 is a side elevation view of the needle holder of the image chamber of FIG. 4.

As shown in FIGS. 4 and 7, needle holder 118 has four openings 144 which are located to match the positions of openings 140 of cover 114. Each pair of openings 140 and 144 are shaped and positioned to allow a screw or bolt (not shown) to pass through for attaching cover 114 and needle holder 118 to each other. When cover 114 and needle holder 118 are attached, ridge 142 abuts needle holder 118, thus defining an enclosed fluid volume between cover 114 and needle holder 118.

Seven through holes 130 are provided in needle holder 118 for receiving and mounting seven needles (not shown) during use. The mounted needles are connected to the fluid volume defined by ridge 142 of cover 112 and needle holder 118, which serves as the fluid source for the needles.

Four slots 134 are also provided in needle holder 118 for receiving and housing four magnets (not shown). The positions of slots 134 match the positions of slots 136 in base 112. These slots 134, 136 are used to mount the magnets for biasing needle holder 118 and window 124 toward each other during use.

Four spacer openings 120 are also provided in needle holder 118, which are shaped and sized to mount four spacers (not shown) during use. The spacers are used to define the minimum distance between needle holder 118 and window 124 during use. A spacer opening 120 may have an internal thread for engaging a threaded end of a spacer (not shown). A spacer opening 120 may be sized to frictionally engage an end of a spacer (not shown).

Needle holder 118 may be transparent.

The operation and use of image chamber 110 are similar to image chamber 10. In this case, however, cover 114 and platform 118 are attached to each other by bolts and nuts (not shown); micro-needles (not shown), one set of magnets (not shown), and spacers (not shown) are detachably mounted on needle holder 118; and another set of magnets are detachably mounted on base 112. The assembled chamber 110 has a generally cylindrical external shape.

EXAMPLES

Example I

Male Wistar rats (weight of approximately 250-300 g) were anaesthetized using pentobarbitone sodium (0.1 ml/100 g, Nembutal™, Abbott Laboratories) and injected with 0.5 ml heparin (Leo Pharmaceuticals™). Livers of the rats were perfused with 3.7% para-formaldehyde at 37° C. for one hour followed by 1 μM fluorescein for 30 min to obtain fixed samples; and excised. Tissue cylinders from liver samples were prepared using an 8 mm diameter coring-tool on a motor-driven tissue coring-device. Liver slices of 1 mm thickness were precision-cut from the samples using a vibratome.

1 mm thick liver slices pre-perfused with fluorescein were perfused with 10% Trypan Blue solution or 100 μM Rhodamine 6G solution in 1×PBS, at room temperature, for 1 hour using a prototype of imaging chamber 10 with seven micro-needles.

The perfusion solution was circulated to the liver slice in the chamber through inlet 26 and outlet 28. The flow rate through inlet 26 and outlet 28 was increased from 0.1 ml/min to 1.0 ml/min at an increment of 0.1 ml/min every 2 minutes to reduce damage to liver slices associated with sudden pressure changes.

Example II

Live staining of the liver slice in the image chamber was imaged using a digital camera (Kodak Easyshare DX6490™).

From the image results obtained with the digital camera, it was found that after one minute of intra-tissue perfusion (ITP), the Trypan Blue solution had penetrated to the bottom of the tissue, as indicated by a blue colored patch appearing on the tissue. The blue colored patch progressively increased in size, indicating gradual penetration of the dye into other regions of the tissue. After 30 minutes of perfusion, the tissue was almost completely stained with Trypan Blue. No significant change in staining area is observed between 30 min and 60 min.

The stained tissue slice was then cut into two equal halves and imaged under a stereomicroscope. From the obtained image, it was observed that the dye had penetrated the entire tissue and stained the cross section of the tissue. However, there remained some regions of the slice that were not stained.

Example III

Live staining of the liver slice in the image chamber was monitored using a confocal Microscope™ (LSM 510™, Carl Zeiss) with a 10× objective lens (Fluorescein excitation: 488 nm; emission: 500-550 nm; Rhodamine 6G excitation: 543 nm; emission: 565-615 nm).

Diffusion behavior in the tissues was studied with Rhodamine 6G and visually monitored in real-time using the imaging chamber and the confocal microscope. Fluorescence from the Rhodamine 6G started to emerge 369 seconds after perfusion was initiated. Consistent with the results observed in Example I, the area of Rhodamine 6G staining progressively increased with perfusion time. After 2951 s of perfusion; approximately half the field of view was stained with the dye. Non-uniformity in staining was observed.

As shown by the above examples, exemplary embodiments of the present invention described herein can facilitate observation and visualization of cellular changes in real-time, while alleviate mass transfer limitations in thick tissue constructs. The exemplary image chamber described herein can be integrated onto any multi-dimensional imaging microscope, live imaging equipment, or other similar imaging devices, as it has a transparent base layer and small thickness. The examples described above clearly indicate that it is feasible to distribute fluids throughout the entire thick tissue slice. The test results showed that embodiments of the present invention can be useful for imaging or bio-imaging large volumes of tissues or tissue constructs.

For example, the needle platform in an image chamber described herein may be used to interface with porous spacing within tissue engineered constructs. The tissue engineered construct may be immobilized between the micro-needle platform and the transparent base layer. The platform and the base layer may be then held in place by the disc magnets. The chamber and the transparent base layer may be designed to fit into commercially available inverted microscopes for ease of incorporation onto any multi-dimensional microscopy platform. The micro-needles act as a substitute for the nutrient delivery vasculatures, thus solving drawbacks of mass transfer limitations that restrict long-term survival of cells and tissues. By precise control of the flow rate and the pressure of the inlet nutrients, nutrients may be uniformly distributed to the entire construct, and the environment in the imaging chamber may be adjusted to closely resemble the hemodynamic environment of a real liver. Thus, embodiments of the present invention can provide perfusion culture and facilitate imaging and study of thick tissue constructs over long periods using currently available imaging devices such as existing cameras and microscopes.

The image chamber may have dimensions that are similar to those of commonly used Petri dishes. An existing Petri dish may be conveniently adapted and used to form an image chamber according to an embodiment of the present invention, as can be understood by those skilled in the art. This allows the image chamber be integrated or incorporated into many multi-dimensional bio-imaging devices or platforms such as confocal laser scanning microscope (CLSM), multi-photon microscope (MPM) or optical coherence tomography (OCT) microscope. This also makes it possible to image individual cells with a high-resolution, and allows continuous perfusion and long-term culture, with real-time monitoring and observation of flow and tissue dynamics. Micro-needles perfusion can enhance uniform distribution of perfusion media, which subsequently ameliorates the viability and functionality of the tissue engineered constructs over a long-term culture.

The needle platform may be produced using suitable microfabrication techniques, which allows the micro-needles be formed in different sizes, array distance and shape. This flexibility may be convenient in some cases.

Embodiments of the present may be used in various applications such as for bio-imaging or in tissue engineering applications.

For example, the imaging chamber may be used for bioimaging and in biological investigations. A transparent base layer allows the chamber to be imaged on many different inverted microscopes with low working distance requirements. A tissue engineered construct can be held tightly in place between the micro-needles and the base layer by the disc magnets, thus immobilizing and avoiding fluid being trapped between the tissue construct and the base layer, which can affect image quality. An exemplary embodiment of the present invention may provide an optimal environment for tissue viability and functions.

The image chamber may be used to continuously perfuse a fluid directly into the inner cores of the tissue. This facilitates precise control of flow rate and pressure in the construct and hence, allows investigation of inter-dependency of hemodynamic environments on cellular behavior.

When integrated with a high-resolution microscopy system, the image chamber may be used to track individual molecule, and to image various transport pathways within a 3D tissue engineered construct online and in real time.

By adjusting the density and the length of micro-needles, the culture tissue slices, and engineered tissue constructs used for imaging may be of relatively large dimensions such as much larger than 1 mm. Tissues or tissue constructs larger than 1 mm tend to disintegrate rapidly if there is limited mass transfer through them. Injected perfusion, using micro-needles, can be precisely controlled to feed nutrients and remove metabolic wastes for efficient functions of cells and maintenance of structural integrity of tissues or tissue constructs with dimensions larger than 1 mm.

The image chamber may also allow imaging or visualization of the culture process in a tissue engineered construct, including cellular dynamics and cell interaction with the surroundings (including neighbouring cells, biomaterial surface and hemodynamic environment). The image chamber can also be integrated onto organotypic tissue slice culture such as liver slice. Various stimulations can be artificially introduced to facilitate the study of processes such as pathogenesis of diseases, angiogenesis and tumorigenesis.

In embodiments of the present invention, the input/output flow rate and pressure may be independently adjusted, and may be conveniently used to investigate the pathology of diseases (such as fibrosis), which may depend on these parameters.

Liver slices may also be a suitable model for studying pathogens infections such as Hepatitis B and C viruses (HBV and HCV), malaria parasite and also colon cancer. The primary site of pathogenesis of malaria infection and colon cancer metastasis is the liver. Thus, the heterogeneity in the liver slice and maintenance of long-term survival of the liver slice using embodiments of the present invention can facilitate investigations of these diseases in the liver.

Liver is the main site for de-toxification. Long-term culture of a liver slice can potentially be used to detect environmental toxins. A bioimaging system incorporating embodiments of the present invention may be used for environmental protection applications and for quick screening against bioterrorism.

Other features, benefits and advantages of the embodiments described herein not expressly mentioned above can be understood from this description and the drawings by those skilled in the art.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A device for imaging a tissue culture, comprising:
   a chamber for housing a tissue to be cultured and imaged therein, said chamber comprising a transparent window;
   a platform facing said window;
   a plurality of micro-needles mounted on said platform and connected for fluid communication with a fluid source;
   said platform and said window magnetically biased toward each other to press said micro-needles into said tissue sandwiched between said window and platform for injecting a fluid into said tissue; and
   a spacer placed between said platform and said window for preventing over-compression of said tissue by said platform and said window.

2. The device of claim 1, wherein said chamber comprises a well-shaped base and a cover for covering said base, said window forming a part of said base.

3. The device of claim 2, comprising a first magnet attached to said platform and a second magnet attached to said base, said first and second magnets attracting each other thus biasing said platform and said window toward each other.

4. The device of claim 3, wherein said first magnet comprises a first set of disc magnets, and said second magnet comprises a second set of disc magnets.

5. The device of claim 2, wherein said base comprises a Petri dish.

6. The device of claim 1, wherein said micro-needles comprise seven needles.

7. The device of claim 1, wherein said spacer has a thickness of about 1 mm.

8. The device of claim 1, wherein said tissue has a thickness of about 1 mm or more.

9. The device of claim 1, comprising an inlet in fluid communication with said needles for supplying a fluid to said tissue, and an outlet for discharging a fluid from said chamber.

10. The device of claim 1, wherein said window is formed of glass.

11. The device of claim 1, wherein said window comprises a transparent polymer.

12. The device of claim 1, wherein said platform is formed of a polymer.

13. The device of claim 1, wherein said spacer is attached to said platform.

14. The device of claim 1, wherein said spacer comprises a plurality of spacers.

15. The device of claim 1, wherein said chamber has a generally cylindrical external shape.

16. A method of operating the device of claim 1, comprising:
    placing a tissue on said window,
    placing said platform on said tissue with said needles contacting said tissue,
    magnetically biasing said platform and said window toward each other, thus pressing said needles into said tissue;
    maintaining a distance between said platform and said window with said spacer;
    supplying a fluid to said tissue through said needles from said fluid source; and
    imaging said tissue through said window.

17. The method of claim 16, comprising discharging a waste fluid from said chamber.

18. The method of claim 16, wherein said imaging comprises imaging said tissue with a camera.

19. The method of claim 16, wherein said imaging comprises imaging said tissue with a microscope.

20. The method of claim 19, wherein said microscope is an inverted microscope.

21. The method of claim 19, wherein said microscope is a confocal microscope.

22. The method of claim 16, wherein said tissue is monitored over a period of time.

* * * * *